(12) United States Patent
Anghel et al.

(10) Patent No.: US 9,035,236 B2
(45) Date of Patent: May 19, 2015

(54) DETECTING HIGH ATOMIC NUMBER MATERIALS WITH COSMIC RAY MUON TOMOGRAPHY

(75) Inventors: Vinicius Anghel, Deep River (CA); Guy Jonkmans, Deep River (CA); Cybele Jewett, Deep River (CA); Martin Thompson, Petawawa (CA)

(73) Assignee: Atomic Energy of Canada Limited, Chalk River, Ontario (CA)

( * ) Notice: Subject to any disclaimer, the term of this patent is extended or adjusted under 35 U.S.C. 154(b) by 0 days.

(21) Appl. No.: 14/124,504

(22) PCT Filed: Jun. 7, 2012

(86) PCT No.: PCT/CA2012/050384
§ 371 (c)(1),
(2), (4) Date: Jul. 30, 2014

(87) PCT Pub. No.: WO2012/167381
PCT Pub. Date: Dec. 13, 2012

(65) Prior Publication Data
US 2014/0332685 A1    Nov. 13, 2014

Related U.S. Application Data

(60) Provisional application No. 61/494,171, filed on Jun. 7, 2011.

(51) Int. Cl.
*G01T 1/00* (2006.01)
*G01T 1/29* (2006.01)
(Continued)

(52) U.S. Cl.
CPC ............ *G01V 5/0025* (2013.01); *G01N 23/046* (2013.01); *G01N 23/20* (2013.01);
(Continued)

(58) Field of Classification Search
CPC ... G01V 5/0025; G01V 5/005; G01V 5/0091; G01V 5/0008; G01V 5/0016; G01N 23/201; G01N 23/046
USPC ......... 250/251, 306, 307, 397, 358.1, 370.09; 382/131, 254
See application file for complete search history.

(56) References Cited

U.S. PATENT DOCUMENTS 7,838,841 B2 * 11/2010 Morris et al. ................ 250/397
7,945,105 B1 *  5/2011 Jaenisch ...................... 382/249
(Continued)

OTHER PUBLICATIONS

Supplementary European Search Report dated Oct. 29, 2014, 6 pages.
(Continued)

*Primary Examiner* — Nikita Wells
(74) *Attorney, Agent, or Firm* — Anderson Gorecki & Rouille LLP (57) ABSTRACT

A method is proposed herein to detect high atomic number materials, such as Special Nuclear Materials, within a container based on muon tomography. The container is modeled as a plurality of volume elements. Information related to an initial trajectory and a final trajectory of each muon passing through the container is received. Additionally, a set of initial outer prong vectors and a set of final outer prong vectors are created. Then, a plurality of vector combinations are created from a selected initial vector and a selected final vector. A metric is determined and associated with each vector combination. A subset of the plurality of vector combinations is associated with each volume element and an estimated scattering density is determined and assigned to the volume element. Based on the estimated scattering density assigned to the volume elements, a three dimensional image of the container may be generated.

12 Claims, 6 Drawing Sheets

(51) Int. Cl.
*G01N 23/083* (2006.01)
*H01J 3/14* (2006.01)
*G01V 5/00* (2006.01)
*G01N 23/04* (2006.01)
*G01N 23/20* (2006.01)
*H01J 37/252* (2006.01)

(52) U.S. Cl.
CPC ........ G01N2223/626 (2013.01); G01V 5/0066 (2013.01); G01V 5/0091 (2013.01); G01N 2223/419 (2013.01); G01V 5/005 (2013.01); H01J 37/252 (2013.01)

(56) References Cited

U.S. PATENT DOCUMENTS 8,288,721 B2 * 10/2012 Morris et al. ................. 250/306
8,536,527 B2 * 9/2013 Morris et al. ................. 250/307
2008/0191133 A1 8/2008 Morris et al.
2013/0238291 A1 * 9/2013 Schultz et al. ................... 703/2

OTHER PUBLICATIONS

Schultz et al., Statistical Reconstruction for Cosmic Ray Muon Tomography, IEE Transactions on Image Processing, vol. 16, No. 8, Aug. 2007, 9 pages.
Debasis Mitra et al., Simulation Study of Muon Scattering for Tomography Reconstruction, 2009 IEE Nuclear Science Symposium Conference Record, Oct. 2009, 5 pages.
Anghel V. et al., Cosmic Ray Muon Tomography System Using Drift Champers for the Detection of Special Nuclear Materials, Nuclear Science Symposium Conference Record (NSS/MIC), IEEE Oct. 2010, 5 pages.
Hengartner et al., Information Extraction for Muon Radiography, 2005 IEE Nuclear Science Symposium Conference Record, Oct. 2005, 5 pages.
XP-002731173, INSPEC/IEE, 2 pages.

* cited by examiner

DETECTING HIGH ATOMIC NUMBER MATERIALS WITH COSMIC RAY MUON TOMOGRAPHY

CROSS-REFERENCE TO RELATED APPLICATION

This application claims the benefit of and priority to U.S. Provisional Patent Application No. 61/494,171 filed Jun. 7, 2011 under the title DETECTING HIGH ATOMIC NUMBER MATERIALS WITH COSMIC RAY MUON TOMOGRAPHY.

The content of the above patent application is hereby expressly incorporated by reference into the detailed description hereof.

FIELD

The present application relates generally to detecting high atomic number materials within containers and, more specifically, to the use of cosmic ray muon tomography for such detection.

BACKGROUND

E.P. George first pioneered the use of cosmic rays to measure the interior of a large structure in 1955, when he used the attenuation of cosmic rays to determine the overburden of the Guthega-Munyang tunnel in New South Wales, Australia. In the late 1960s, Luis Alvarez et al. then used measurements of the attenuation of cosmic ray muons to search for chambers within Chephren's pyramid. In response to post 9/11 concerns that terrorists might attempt to smuggle illicit nuclear materials or bombs via ports of entry, groups at Los Alamos National Laboratory and Uppsala University in Sweden have explored the use of cosmic ray muon tomography to detect Special Nuclear Materials (SNM) hidden within cargo containers.

BRIEF DESCRIPTION OF THE DRAWINGS

Reference will now be made, by way of example, to the accompanying drawings which show example implementations; and in which.

DETAILED DESCRIPTION

Figure 1:
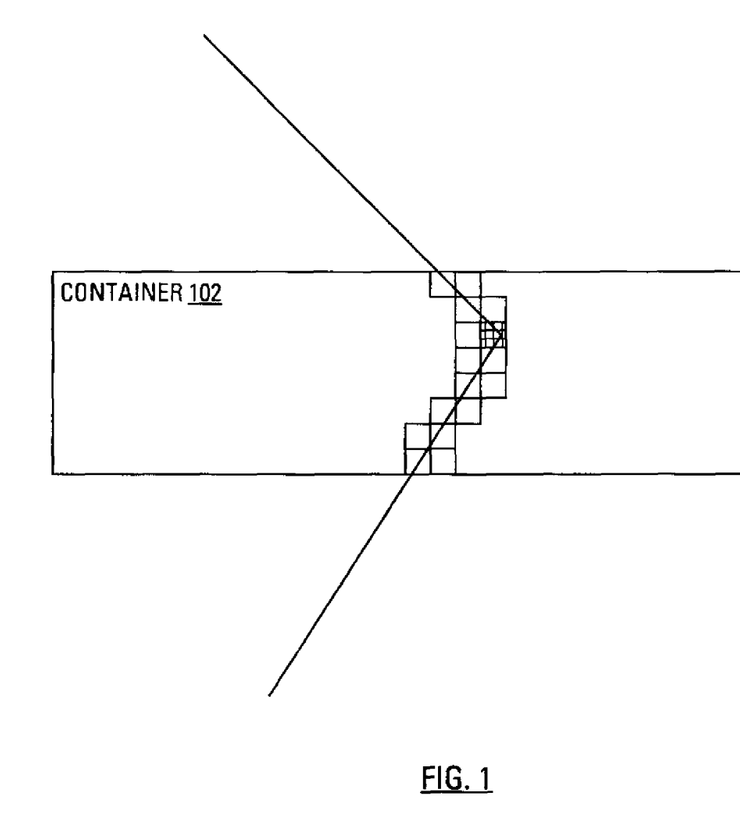
FIG. 1 illustrates a container hidden within which Special Nuclear Materials are to be detected.

FIG. 1 illustrates a container 102 hidden within which Special Nuclear Materials are to be detected.

As a given muon passes through a tracker plane 104, the tracker plane 104 records a "muon hit position". For a given muon, a muon hit position in the first tracker plane 104-1 and a muon hit position in the second tracker plane 104-2 provide points that define an "initial trajectory vector". For the same given muon, a muon hit position in the third tracker plane 104-3 and a muon hit position in the fourth tracker plane 104-4 provide points that define a "final trajectory vector".

Within the container 102, it is anticipated that the given muon will reflect many times as it passes through an object. However, the points at which the given muon scatters most strongly are typically located within the higher atomic number, higher density regions of the object. It is for this reason that the points determined in a Point of Closest Approach (PoCA) analysis of a number of muons have been found to provide good indicators of the locations of high atomic number, high density materials, like SNM, especially if such materials are surrounded by a lot of much lower density material.

Most existing SNM identification algorithms are based on a conjoint use of a PoCA for the geometry of the particle trajectory and a Maximum Likelihood/Expectation Maximization approach (ML/EM) for a statistical identification.

Unfortunately, The ML/EM approach is based on a slowly-converging iterative method and may be considered to require considerable computing resources.

Unlike the X-ray, γ-ray and neutron beams, all of which have been investigated for SNM detection, cosmic-ray muons are a naturally occurring, harmless form of penetrating radiation. Muons are produced in the Earth's upper atmosphere when cosmic ray protons collide with air molecules. Muons are leptons and have the same properties as electrons, except that muons are much more massive (about 207 $m_e$) and have a lifetime of only 2.2 μs. Cosmic ray muons arrive at the surface of the Earth at a rate of about 1/cm²/min, and have a mean energy of 3-4 GeV. The relativistic speeds of cosmic ray muons thus allow them to live long enough to reach the Earth's surface and to penetrate several meters of rock.

When muons travel through a material, such as rock, each muon reflects many times off the electrons and protons in the material. The muons that survive passage through the material emerge with a distribution of cumulative scattering angles, θ, that is given by the following equation:

$$\sigma_\theta = \frac{13.6 \text{ MeV}}{\beta c p} \sqrt{\frac{H}{X_0}\left[1 + 0.038\ln\left(\frac{H}{X_0}\right)\right]}. \quad \text{Equation 1}$$

where H is the distance the muon traveled through the material and $\sigma_\theta$ is the standard deviation of the cumulative scattering angle distribution. 98% of the cumulative scattering angles of a collection of muons are expected to coincide with a Gaussian distribution having a standard deviation $\sigma_\theta$. The remaining 2% of the cumulative scattering angles are expected to lie in broad non-Gaussian tails. The quantity $X_0$ is the radiation length of the material, which radiation length decreases with increasing material density and atomic number, Z. Accordingly, muons traversing a block of low-Z material will tend to have smaller cumulative scattering angles than those muons traversing a lump of high-Z material. An example high-Z material is uranium. It has been determined that, if one determines the cumulative scattering angles of a collection of muons that have passed through a container, one can use the scattering angles of the muons to determine whether low, medium or high-Z material is inside the container.

By using the known Points of Closest Approach Method, one can estimate the positions of different materials within a container. A PoCA may be defined as a point at which the initial trajectory and the final trajectory are closest to each other. In view of FIG. 2, a connecting line 208 may be defined to connect an initial trajectory vector 206 to a final trajectory vector 210. The PoCA 212 is at the midpoint of the line 208. The line 208 is perpendicular to the initial trajectory vector 206 and the final trajectory vector 210. However, due to the limitations of a two-dimensional drawing, the line 208 may not appear to be perpendicular to the two trajectory vectors. Given the initial trajectory vector 206 and the final trajectory vector 210, one can determine the PoCA 212. One can obtain the initial trajectory vector 206 and the final trajectory vector 210 of a muon that passed through the container 202, by placing at least two tracker planes above the container 202 and at least two tracker planes below the container 202 as illustrated in FIG. 1.

Figure 2:
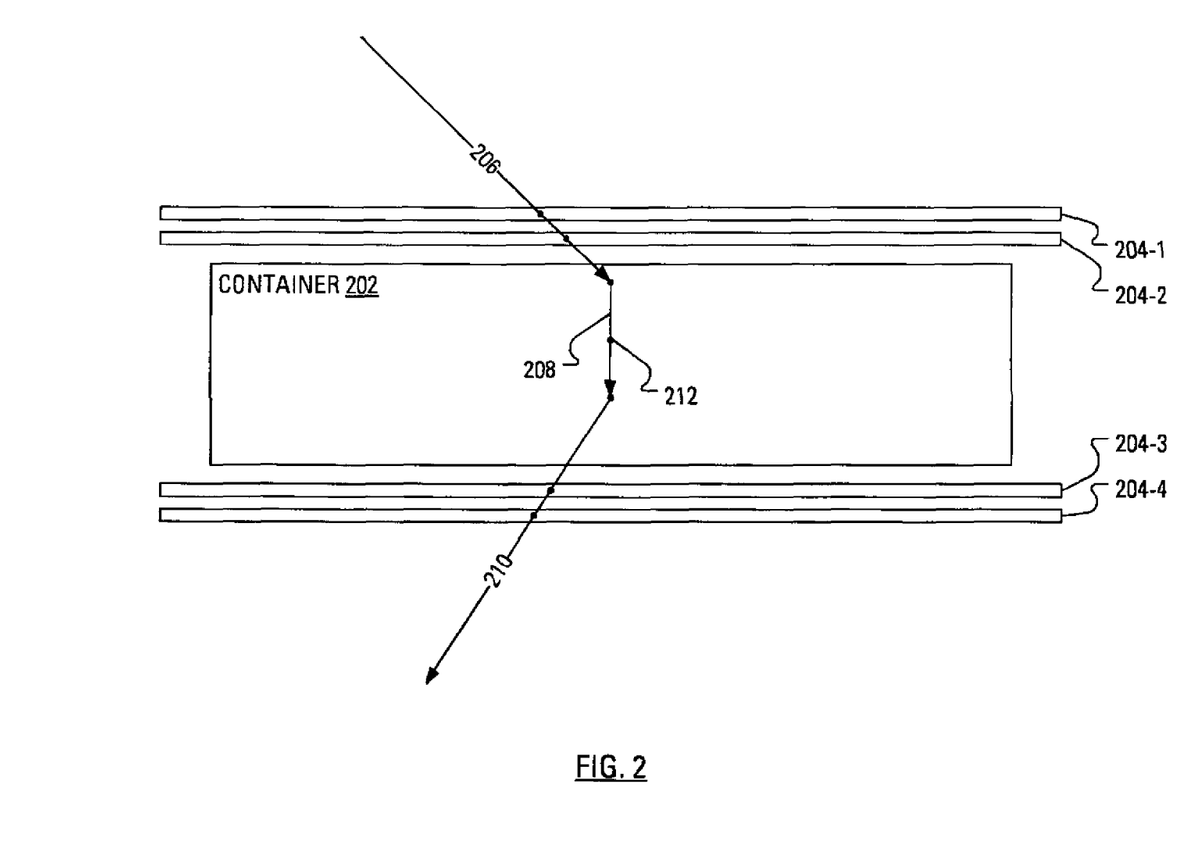
FIG. 2 illustrates a cargo container with tracking planes positioned above and below the cargo container.

In general, the path of a given muon through the container may be described with a "four-point track", as illustrated in FIG. 2. FIG. 2 illustrates a cargo container 202. A first tracker plane 204-1 is positioned above the cargo container 202. A second tracker plane 204-2 is positioned above the cargo container 202 and below the first tracker plane 204-1. A fourth tracker plane 204-4 is positioned below the cargo container 202. A third tracker plane 204-3 is positioned below the cargo container 202 and above the fourth tracker plane 204-4. The tracker planes (which may be referred to individually or collectively by reference numeral 204) may be broadly described as position-sensitive radiation detectors.

The four-point track for a muon is defined by: a first point, at which the muon passes through the first tracker plane 204-1; a second point, at which the muon passes through the second tracker plane 204-2; a third point, at which the muon passes through the third tracker plane 204-3; and a fourth point, at which the muon passes through the fourth tracker plane 204-4. The first point and the second point define an initial trajectory 206. The third point and the fourth point define a final trajectory 210.

A method is proposed herein to detect, based on muon tomography, high atomic number materials, such as Special Nuclear Materials, within a container. Conveniently, the proposed method is direct, in that the proposed method does not involve iteration. Based on the detection, an image of the container may be generated with an indication of contents with high atomic number materials, if any are present.

In signal detection theory, a receiver operating characteristic (ROC), or simply ROC curve, is a graphical plot of the sensitivity, or true positive rate, vs. false positive rate, for a binary classifier system responsive to variations in a discrimination threshold of the binary classifier system. ROC curves generated based on the operation of aspects of the present application have indicated that the aspects are suitable for their intended purpose.

According to an aspect of the present disclosure, there is provided a method of detecting high atomic number materials within a container. The method includes modeling the container as a plurality of volume elements. The method further includes, for each muon of a plurality of muons passing through the container: receiving information related to an initial trajectory of each muon; receiving information related to a final trajectory of each muon; creating, based on an initial trajectory vector formed based on the information related to the initial trajectory, a set of initial outer prong vectors; creating, based on a final trajectory vector formed based on the information related to the final trajectory, a set of final outer prong vectors; creating a plurality of vector combinations. The plurality of vector combinations are created from: a selected initial vector, selected from among the initial trajectory vector and the set of initial outer prong vectors; and a selected final vector, selected from among the final trajectory vector and the set of final outer prong vectors. The method further comprises, for each vector combination of the plurality of vector combinations, determining a metric, associating the metric with each vector combination. The method further comprises, for each volume element of the plurality of volume elements, determining a subset of the plurality of vector combinations to associate with each volume element, determining an estimated scattering density based on the metrics associated with the subset of the plurality of vector combinations, assigning the estimated scattering density to each volume element. The method further comprises, based on the estimated scattering density assigned to each volume element, generating a three dimensional image of the container. In other aspects of the present application, a processor is provided for carrying out this method and a computer readable medium is provided for adapting a processor to carry out this method.

Other aspects and features of the present disclosure will become apparent to those of ordinary skill in the art upon review of the following description of specific implementations of the disclosure in conjunction with the accompanying figures.

Scattering density, λ, is a measure of the ability of a material to produce large deflections in a trajectory of a muon. A definition of the scattering density, based on Equation 1, is given by $$\lambda = \left[\frac{13.6 \text{ MeV}}{(\beta c p)_0}\right]^2 \frac{1}{X_0}.$$

where $(\beta c p)_0$ is the average of the product of the muons' speeds and momenta. As one can see, the scattering density, λ, increases with decreasing $X_0$. Hence, high-Z materials, like uranium, which have shorter radiation lengths, will have larger scattering densities than low to mid-Z materials, like aluminum and iron. Thus, a three dimensional (3D) map of the scattering density inside a container can act as a 3D map of the mass density and atomic number of materials within the container. Since the logarithmic term in Equation 1 is generally no larger than about 0.17, compared to unity, one can choose to neglect the logarithmic term. Thus, after neglecting the logarithmic term, if one substitutes Equation 1 into Equation 2, one obtains a definition for the scattering density in terms of the quantities that may be measured with tracker modules and a momentum spectrometer:

$$\lambda = \frac{\sigma_\theta^2}{H}\left[\frac{\beta c p}{(\beta c p)_0}\right]^2.$$

Such a definition has been proposed in Larry Schultz et al., "ML/EM Reconstruction Algorithm for Cosmic Ray Muon Tomography", *IEEE Nuclear Science Symposium Conference Record*, M11-190. The quantity H, in this case, is an estimate of the length of the muon's path through the material and βcp is the product of the muon's speed and momentum. A momentum spectrometer may be used to provide this speed-momentum product information. One can obtain an estimate of H from the muon's scattering angle and the length of the line passing through the PoCA, and connecting the muon's initial trajectory to the muon's final trajectory. Finally, $\sigma_\theta^2$ is estimated with the muon's cumulative scattering angle, $\theta^2$.

Figure 3:
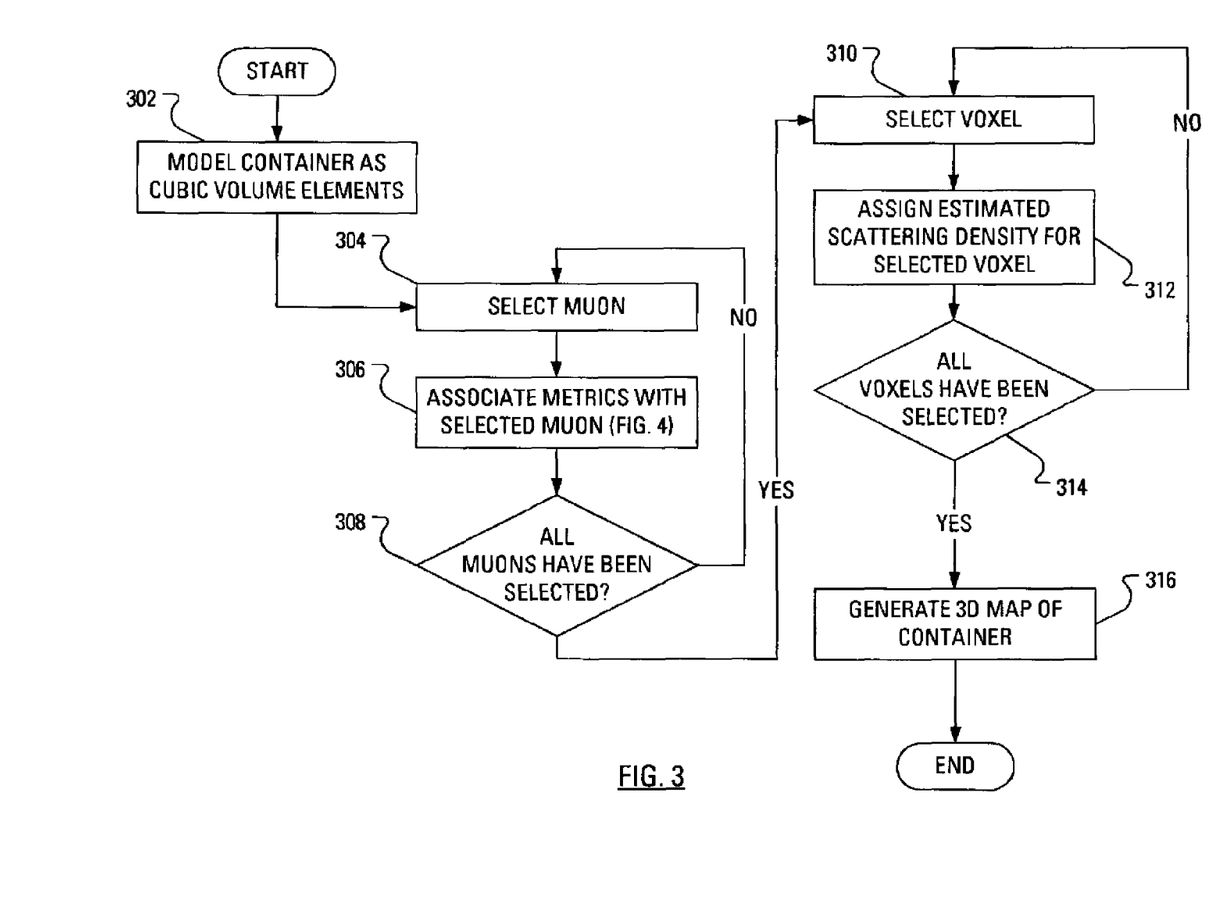
FIG. 3 illustrates example steps in a method of generating an estimated scattering density 3D map of a cargo container in accordance with aspects of the present application.

FIG. 3 illustrates example steps in a method of generating an estimated scattering density 3D map of a cargo container.

The method may be considered to be arranged for execution by a processor (not shown) in a computer system (not shown). More particularly, the method may be considered to act upon a data set comprising, for each muon of a plurality of muons that have entered a container of interest over the course of a measurement period, muon hit position information that defines an initial trajectory vector and a final trajectory vector.

An initial step involves modelling (step 302) a container of interest as being divided into a plurality of cubic volume elements, called "voxels". An example voxel dimension is 1000 cm$^3$. Once the cargo container has been modelled as a collection of voxels, the processor may select (step 304) a muon from among the plurality of muons for which there exists data in the data set. The processor may then associate (step 306) a set of metrics with the selected muon.

Figure 4:
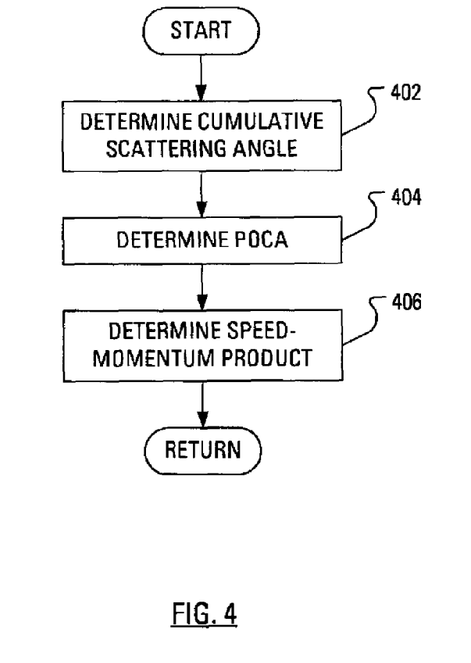
FIG. 4 illustrates example steps in a method of associating metrics with a selected muon, as part of the method of FIG. 3, in accordance with aspects of the present application.

FIG. 4 illustrates example steps in a method of associating metrics with a selected muon. The processor determines (step 402) a cumulative scattering angle, $\theta^2$, for the selected muon. In one manner of determining a cumulative scattering angle, a dot product is obtained for an initial trajectory vector and a final trajectory vector. It is known that the dot product provides the cosine of the angle between the two vectors. To obtain the cumulative scattering angle, the processor obtains the inverse cosine of the dot product.

The processor also constructs a four-point track (see FIG. 2) for the selected muon, thereby allowing the processor to determine (step 404) a PoCA for the selected muon. The processor also determines (step 406) a speed-momentum product for the selected muon.

Once, metrics have been associated (step 306) with the selected muon, the processor may then determine (step 308) whether there exists data in the data for further muons. Upon determining (step 308) that all muons have been considered, the processor may proceed to consideration of the voxels.

Such consideration begins with selecting (step 310) a voxel. The processor may then assign (step 312), to the selected voxel, an estimated scattering density. More particularly, the processor may analyze the metrics associated with the muons to select a set of muons that had a respective PoCA inside the selected voxel. The processor may then base the estimated scattering density for the selected voxel upon the cumulative scattering angles, cumulative momenta and cumulative distances between the PoCA points of the selected set of muons. Further particularly, the processor may determine an average of the cumulative scattering angles, cumulative momenta and cumulative distances between the PoCA points for the selected set of muons.

Such averaging may be seen to result in errors in angular resolution. Such errors may be seen to lead to some poorly localized "hot spots", where the deflection angle and/or PoCA distance are relatively high. A "Pitchfork" Method reduces the influence of such hotspots by "spreading" the hotspots according to the angular resolution of the measuring process. It has been found empirically that "real" points are less affected by errors in localization and, hence, the real points are less likely to be less "spread out".

After having assigned (step 312) an estimated scattering density to the selected voxel, the processor may determined (step 314) whether there are further voxels to consider. Upon determining (step 314) that there are further voxels to consider, the processor may return to select (step 310) a voxel that has not been previously considered. Upon determining (step 314) that there are no further voxels to consider, the processor may proceed to generate (step 316) a 3D map of the container, based on a value for the scattering density assigned to each of the voxels.

Figure 5:
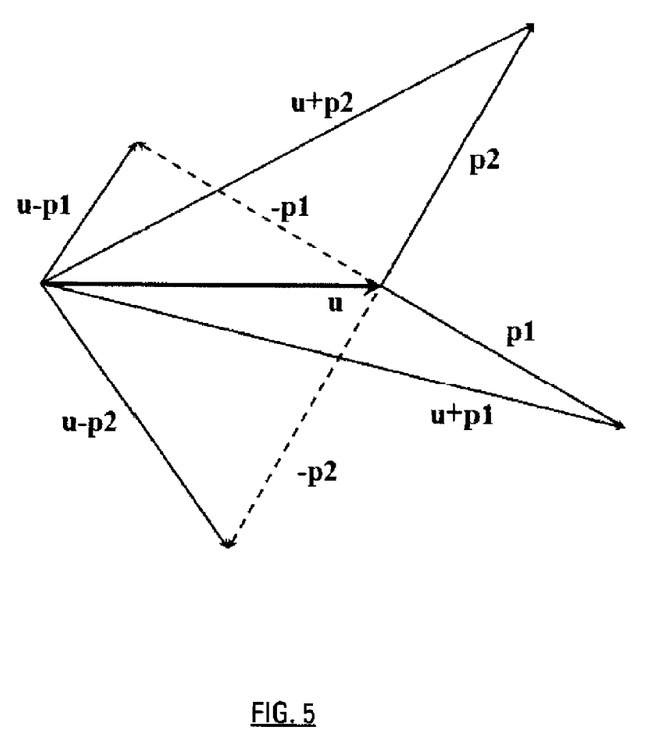
FIG. 5 illustrates a set of vectors useful in describing a "Pitchfork Method"

FIG. 5 illustrates a set of vectors useful in describing the Pitchfork Method. The base vector to which all the other vectors relate is associated with reference character u. The base vector u is representative of either an initial trajectory vector or a final trajectory vector. When executing the Pitchfork Method, the processor creates two randomly-oriented, perpendicular vectors of magnitude one. In FIG. 5 these vectors are associated with reference characters p1 and p2. When executing the Pitchfork Method, the processor also creates four outer prongs of a figurative pitchfork by adding and subtracting vector p1 and vector p2 from the base vector, u.

When determining (step 402, FIG. 4) a cumulative scattering angle, $\theta^2$, for a selected muon, the processor uses the top base vector u or one of its four outer prong vectors, and the bottom base vector u or one of its four outer prong vectors. Similarly, when determining (step 404, FIG. 4) a PoCA for a selected muon, the processor uses the top base vector u or one of its four outer prong vectors, and the bottom base vector u or one of its four outer prong vectors.

In all, there is one initial trajectory vector and four outer prong vectors associated with the initial trajectory vector, for a total of five initial vectors, additionally, there is one final trajectory vector and four outer prong vectors associated with the final trajectory vector, for a total of five final vectors. The processor may create vector combinations by combining an initial vector with a final vector. The processor may select the initial vector from among the initial trajectory vector and the set of initial outer prong vectors. The processor may select the final vector from among the final trajectory and the set of final outer prong vectors. In the present example, the processor creates 25 vector combinations. Accordingly, the processor may determine (step 402, FIG. 4) 25 cumulative scattering angles, $\theta^2$, for a selected muon. Similarly, the processor may determine (step 404, FIG. 4) 25 PoCAs for a selected muon.

When the processor determines an average for a given voxel, the processor may be configured to give a smaller weight to PoCAs and cumulative scattering angles that were determined based on vector combinations that use at least one outer prong vector. Correspondingly, the processor may be configured to give a larger weight to PoCAs and cumulative scattering angles that were determined based on vector combinations that use the base vectors. Hence, PoCAs and cumulative scattering angles determined based on a vector combination of the two base vectors may, for instance, be given a weight of 1/9. PoCAs and cumulative scattering angles calculated based on vector combinations that use one base vector and one outer prong vector may be given a weight of 1/18 and PoCAs and cumulative scattering angles determined based on vector combinations of two outer prong vectors may be given a weight of 1/36.

Using the Pitchfork method, the processor may analyze the metrics associated with the vector combinations to select a set of vector combinations that are associated with a respective PoCA inside the selected voxel. The processor may then base the estimated scattering density for the selected voxel upon the cumulative scattering angles, cumulative momenta and cumulative distances between the PoCA points of the selected set of vector combinations. Further particularly, the processor may determine an average of the cumulative scattering angles, cumulative momenta and cumulative distances between the PoCA points for the selected set of vector combinations.

Finally, the processor may be configured to discard all of the vector combinations for which the product of the muon momentum (p) and the scattering angle ($\theta$) is greater than a threshold. The threshold may, for example, be a comparative threshold such a threshold value that is greater than the momentum/angle product for 98% of the vector combinations. The processor may act thus to remove the non-Gaussian outliers. It may be shown that a presence of non-Gaussian outliers can tend to increase the difficulty of discriminating between mid-Z materials and high-Z materials. While 98% has been successfully used in the determining the threshold, it should be clear that other, similar, values would also lead to reasonable results.

It is proposed herein to use a Monte Carlo particle transport simulation code, such as GEANT4 (see geant4.cern.ch), which was developed by an international collaboration based at Conseil Européen pour la Recherche Nucléaire (CERN), to simulate the passage of muons through a cargo container. The simulation code incorporates three main simulation modules: a Geometry module; an Event Generator module; and an Event Recorder module. The Geometry module provides control over simulation geometry and materials used in the creation of the simulation geometry. The Event Generator module generates primary particles that are specified by the user, and secondary particles, generated by interactions of the primary particles with matter. The Event Generator module provides control not only over the primary particle species, but also over the particles' energies, momentum vectors and positions of origination. Once the Event Generator module throws a particle into the simulation, the Event Generator module uses the physics processes associated with that particle to determine the behaviour of that particle. Since the user must specify the processes that will apply to each particle species generated, the simulation code also provides the user with control over the physics that will be simulated. Finally, the Event Recorder module provides output to the screen and/or a file of the data generated by the simulation. As in the cases of the Geometry module and the Event Generator module, the simulation code also gives control over what information is recorded in an output file or printed to the screen.

Figure 6:
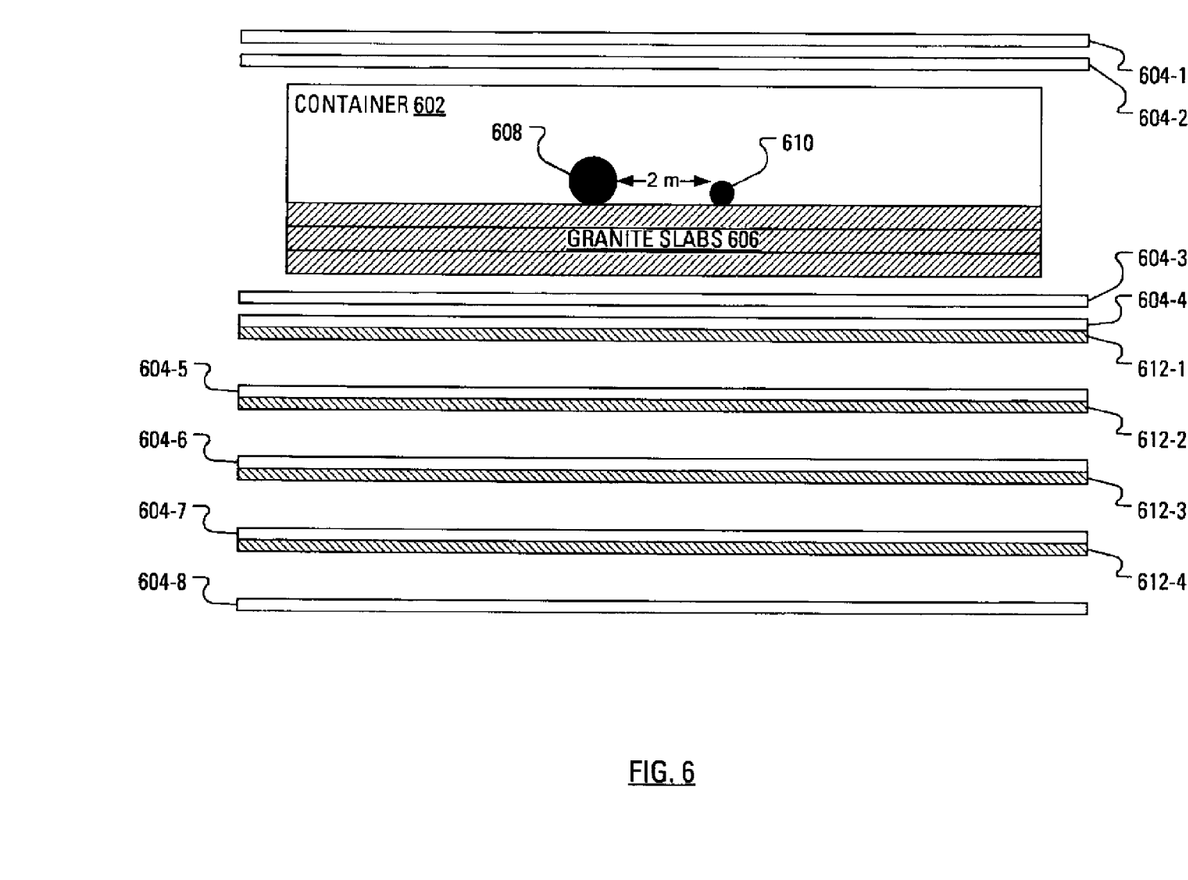
FIG. 6 geometry used in a simulation of aspects of the present application.

Simulation geometry is illustrated in FIG. 6, including a cargo container 602 with steel walls 3 mm thick. The cargo container 602 was simulated to hold a 26 cm tall stack of granite slabs 606, a 25 kg Highly Enriched Uranium (HEU) sphere 608 and an 8 kg HEU sphere 610. The spheres 608, 610 were simulated to be surrounded by 2.8 cm thick spherical, lead shields (not specifically shown). A first tracker plane 604-1 is positioned above the cargo container 602. A second tracker plane 604-2 is positioned above the cargo container 602 and below the first tracker plane 604-1. A fourth tracker plane 604-4 is positioned below the cargo container 602. A third tracker plane 604-3 is positioned below the cargo container 602 and above the fourth tracker plane 604-4. The tracker planes (which may be referred to individually or collectively by reference numeral 604) were simulated to be formed of two 1.7 cm thick, polystyrene slabs of density 1.06 g/cm³.

The centers of the tracker planes 604 were simulated to be 1 m apart. The second tracker plane 604-2 was simulated to be 50 cm above the cargo container 602. The third tracker plane 604-3 was simulated to be 50 cm below the cargo container 602. Each tracker plane 604 was simulated to extend 50 cm beyond the cargo container's front, back and side faces.

The simulation geometry also included a muon momentum spectrometer. The muon momentum spectrometer was simulated as four further tracker planes (a fifth tracker plane 604-5, a sixth tracker plane 604-6, a seventh tracker plane 604-7 and an eighth tracker plane 604-8) and four 10 cm thick iron slabs (a first iron slab 612-1, a second iron slab 612-2, a third iron slab 612-3 and a fourth iron slab 612-4, collectively or individually referenced as 612). Each combination of tracker plane 604 over iron slab 612 was simulated as being placed 1 m away from the next combination of tracker plane 604 over iron slab 612.

In order to accurately depict the cosmic ray muons that were incident upon the tracker planes 604 and the cargo container 602, the polar angles of the initial muon trajectories were drawn randomly from a $\cos^2\theta$ distribution. The initial energy assigned to each muon was then randomly taken from the µ+ energy spectrum measured with the Balloon-borne Experiment with a Superconducting Spectrometer (BESS) at Tsukuba, Japan. Most of the simulated muons had energies below 2 GeV. Larger muon energies are more common at larger zenith angles and the BESS distribution was taken for vertically-oriented muons. Hence, by using the BESS spectrum to represent muons of all zenith angles, the simulations underestimated the number of higher energy muons. Nevertheless, since only a small fraction of the muons had zenith angles greater than 45°, the use of the BESS spectrum was considered to represent a reasonable approximation.

The last aspect of the simulations involved the processes each muon underwent in its travels through the simulated geometry. The four muon processes that were simulated were G4MuMultipleScattering, G4MuIonisation, G4MuBremsstrahlung and G4MuPairProduction. G4MuMultipleScattering, as the name suggests, is the process of multiple elastic scattering of muons off of the electrons and nuclei in the object they are traversing. This process is based on the Urban Multiple Scattering Model90 and the Wentzel Model, which contain empirical correction terms to Equation 1. G4MuIonisation is representative of the muon energy loss process in which a muon imparts enough energy to an electron to cause the electron to leave the atom to which the electron was attached. This is a form of inelastic muon scattering on atomic electrons. G4MuBremsstrahlung is the process by which a muon radiates energy as it decelerates. The bremsstrahlung energy that a decelerating charged particle emits is in the form of X-rays. Finally, G4MuPairProduction is the process in which a muon creates a positron-electron pair while travelling through an object. All four of these processes have an impact on the energy loss of a muon as it travels through matter; however, the process that has the greatest effect on the cumulative scattering angle of the muon is multiple scattering. Since the inelastic scattering of muons on nuclei is important only for muons above 10 GeV and most of the simulated muons had energies below that value, inelastic nuclear scattering was not simulated. Since the muon nuclear spallation reaction cross sections are many orders of magnitude smaller than those for the simulated processes, they were not included in the simulations.

The reconstructed images identify SNM successfully for simulated detectors with 1 mm horizontal position resolution. They also indicate that two minutes of muon exposure are required for reliable identification of the lead-shielded 25 and 8 kg spheres of Highly Enriched Uranium (HEU) that were simulated.

Proposals put forth in the present application include several particular aspects. In one aspect, the proposed method is direct, in that the proposed method does not involve any iteration processes. In another aspect, to incorporate measurement errors for the particle trajectory, the processor uses a bundle of N initial vectors combined with a bundle of N final vectors. There are N×N vector combinations. A probability may be associated with each of the N×N vector combinations so that the determined standard deviations for initial vectors and final vectors match the standard deviations determined empirically for the apparatus. In a further aspect, high angular deviations are removed to allow for an analysis involving only small angle particle scattering. Such large deviations can be due to processes (Rutherford scattering) for which the disclosed method may not apply. In a still further aspect, only the PoCA region of the trajectory contributes to the SNM identification. For each voxel, the angular deflection statistics and PoCA distances are used to generate the scattering density. In an even further aspect, to improve the SNM identification, a method of background subtraction and cluster summing is applied. The background subtraction and cluster summing method is pursued independently for each horizontal two-dimensional voxel layer.

Conveniently, aspects of the present application account explicitly for part of the particle trajectory uncertainty. Further conveniently, aspects of the present application conjointly use the statistics of the PoCA distances and the statistics of angular deviation. Still further conveniently, aspects of the present application employ background subtraction and cluster summing.

The above-described implementations of the present application are intended to be examples only. Alterations, modifications and variations may be effected to the particular implementations by those skilled in the art without departing from the scope of the application, which is defined by the claims appended hereto.

What is claimed is:

1. A method of detecting high atomic number materials within a container, said method comprising:
   modeling said container as a plurality of volume elements;
   for each muon of a plurality of muons passing through said container:
      receiving information related to an initial trajectory of said each muon;
      receiving information related to a final trajectory of said each muon;
      creating, based on an initial trajectory vector formed based on said information related to said initial trajectory, a set of initial outer prong vectors;
      creating, based on a final trajectory vector formed based on said information related to said final trajectory, a set of final outer prong vectors;
      creating a plurality of vector combinations from:
         a selected initial vector, selected from among said initial trajectory vector and said set of initial outer prong vectors; and
         a selected final vector, selected from among said final trajectory vector and said set of final outer prong vectors;
   for each vector combination of said plurality of vector combinations:
      determining a metric;
      associating said metric with said each vector combination;
   for each volume element of said plurality of volume elements:
      determining a subset of said plurality of vector combinations to associate with said each volume element;
      determining an estimated scattering density based on said metrics associated with said subset of said plurality of vector combinations;
      assigning said estimated scattering density to said each volume element; and
   based on said estimated scattering density assigned to said each volume element, generating a three dimensional image of said container.

2. The method of claim 1 wherein said volume elements are cubic.

3. The method of claim 1 wherein said metric comprises a cumulative scattering angle.

4. The method of claim 1 wherein said metric comprises a point of closest approach of said selected initial vector to said selected final vector.

5. The method of claim 4 wherein said determining said subset of said plurality of vector combinations to associate with said each volume element comprises determining which vector combinations among said plurality of vector combinations for which said associated point of closest approach is located within said volume element.

6. The method of claim 1 wherein said metric comprises a product of a speed of said each muon associated with said each vector combination and a momentum of said each muon associated with said each vector combination.

7. The method of claim 1 wherein said initial trajectory vector and said final trajectory vector are considered based vectors and said initial outer prong vectors and said final outer prong vectors are collectively considered outer prong vectors and said method further comprises associating said metric determined based on said each vector combination of said base vectors a higher weight than said metric determined based on said vector combination of one of said base vectors and one of said outer prong vectors.

8. The method of claim 7 further comprising associating said metric determined based on said vector combination of said one of said base vectors and said one of said outer prong vectors a higher weight than said metric determined based on said each vector combination of two of said outer prong vectors.

9. The method of claim 1 further comprising:
   for said each vector combination, determining a product of muon momentum and scattering angle;
   determining a threshold value for said product; and
   removing from consideration those vector combinations for which said product exceeds said threshold.

10. The method of claim 9 further comprising determining said threshold value for said product such that 98% of said products determined for said vector combinations are less than said threshold value.

11. An apparatus for detecting high atomic number materials within a container, said apparatus comprising:
   a first position-sensitive radiation detector positioned above said container;
   a second position-sensitive radiation detector positioned between said container and said first position-sensitive radiation detector;
   a third position-sensitive radiation detector positioned below said container;
   a fourth position-sensitive radiation detector positioned between said container and said third position-sensitive radiation detector;
   a processor adapted to:
      model said container as a plurality of volume elements;
      for each muon of a plurality of muons detected by said position-sensitive radiation detectors as passing through said container:
         receive, from said first position-sensitive radiation detector and said second position-sensitive radiation detector, information related to an initial trajectory of said each muon;
         receive, from said third position-sensitive radiation detector and said fourth position-sensitive radiation detector, information related to a final trajectory of said each muon;

create, based on an initial trajectory vector formed based on said information related to said initial trajectory, a set of initial outer prong vectors;
create, based on an initial trajectory vector formed based on said information related to said initial trajectory, a set of final outer prong vectors;
create a plurality of vector combinations from:
   a selected initial vector, selected from among said initial trajectory and said set of initial outer prong vectors; and
   a selected final vector, selected from among said final trajectory and said set of final outer prong vectors;
for each vector combination of said plurality of vector combinations:
   determine a metric;
   associate said metric with said each vector combination;
for each volume element of said plurality of volume elements:
   determine a subset of said plurality of vector combinations to associate with said each volume element;
   determine an estimated scattering density based on said metrics associated with said subset of said plurality of vector combinations;
   assign said estimated scattering density to said each volume element; and
based on said estimated scattering density assigned to said each volume element, generate a three dimensional image of said container.

12. A computer-readable medium containing computer-executable instructions that, when performed by a processor, cause said processor to:
model said container as a plurality of volume elements;
for each muon of a plurality of muons passing through said container:
   receive information related to an initial trajectory of said each muon;
   receive information related to a final trajectory of said each muon;
   create, based on an initial trajectory vector formed based on said information related to said initial trajectory, a set of initial outer prong vectors;
   create, based on a final trajectory vector formed based on said information related to said final trajectory, a set of final outer prong vectors;
   create a plurality of vector combinations from:
      a selected initial vector, selected from among said initial trajectory vector and said set of initial outer prong vectors; and
      a selected final vector, selected from among said final trajectory vector and said set of final outer prong vectors;
for each vector combination of said plurality of vector combinations:
   determine a metric;
   associate said metric with said each vector combination;
for each volume element of said plurality of volume elements:
   determine a subset of said plurality of vector combinations to associate with said each volume element;
   determine an estimated scattering density based on said metrics associated with said subset of said plurality of vector combinations;
   assign said estimated scattering density to said each volume element; and
based on said estimated scattering density assigned to said each volume element, generate a three dimensional image of said container.

* * * * *